United States Patent [19]

Teutsch et al.

[11] 4,232,015
[45] * Nov. 4, 1980

[54] NOVEL Δ⁴-ANDROSTENES

[75] Inventors: Jean G. Teutsch, Pantin; Roger Deraedt, Les Pavillons-sous-Bois, both of France

[73] Assignee: Roussel Uclaf, Paris, France

[*] Notice: The portion of the term of this patent subsequent to Sep. 18, 1996, has been disclaimed.

[21] Appl. No.: 63,939

[22] Filed: Aug. 6, 1979

[30] Foreign Application Priority Data

Aug. 16, 1978 [FR] France .................................. 78 23851

[51] Int. Cl.³ ............................................... C07J 1/00
[52] U.S. Cl. ............................. 424/243; 260/397.45; 260/397.5; 260/239.55 R
[58] Field of Search ............................. 424/241, 243; 260/397.45; /Steroids MS File

[56] References Cited

U.S. PATENT DOCUMENTS

| 3,442,918 | 5/1969 | Feather et al. | 260/239.55 C |
| 4,168,306 | 9/1979 | Teutsch et al. | 260/239.55 C |

Primary Examiner—Elbert L. Roberts
Attorney, Agent, or Firm—Hammond & Littell, Weissenberger and Muserlian

[57] ABSTRACT

Novel Δ⁴-androstenes of the formula

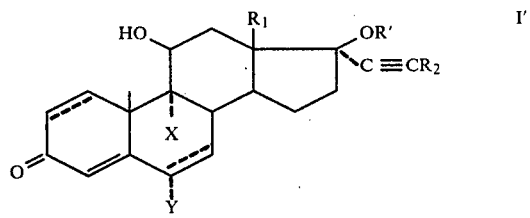

wherein $R_1$ is alkyl of 1 to 3 carbon atoms, R' is an acyl of an organic carboxylic acid or carbonic acid of 1 to 18 carbon atoms, $R_2$ is selected from the group consisting of alkyl of 1 to 12 carbon atoms, alkenyl of 2 to 12 carbon atoms, —$CF_3$, aryl of 6 to 12 carbon atoms and aralkyl of 7 to 12 carbon atoms, Y is selected from the group consisting of hydrogen, fluorine and methyl, X is selected from the group consisting of hydrogen, chlorine, bromine and fluorine and the dotted lines in the A and B rings indicate one or 2 double bonds in 1(2) and 6(7) positions with the proviso when $R_1$ is methyl and the B ring is saturated, X is hydrogen when Y is hydrogen and X is not hydrogen when Y is fluorine having a remarkable anti-inflammatory activity and their preparation.

33 Claims, No Drawings

NOVEL Δ⁴-ANDROSTENES

STATE OF THE ART

U.S. Pat. No. 2,740,798 and No. 3,308,025 describe 11β-hydroxy-17α-ethynyl-steroids which are not substituted in the 17α-position as are the compounds of formula I. U.S. Pat. No. 3,793,308 names 21-methyl-Δ⁴-pregnene-11β,17β-diol-20-yne-3-one but there is no description of how to prepare the compound. U.S. Pat. No. 3,127,428 and No. 3,221,033 have extremely large generic formulas. Other related prior art includes U.S. Pat. No. 3,010,957 and French Pat. No. 1,349,113 and commonly assigned U.S. patent application Ser. No. 878,907 filed Feb. 17, 1978, now U.S. Pat. No. 4,168,306.

OBJECTS OF THE INVENTION

It is an object of the invention to provide the novel Δ⁴-androstenes of formula I' and a process for their preparation.

It is another object of the invention to provide novel anti-inflammatory compositions and to provide a novel method of relieving inflammation in warm-blooded animals.

These and other objects and advantages of the invention will become obvious from the following detailed description.

THE INVENTION

The novel Δ⁴-androstenes of the invention have the formula

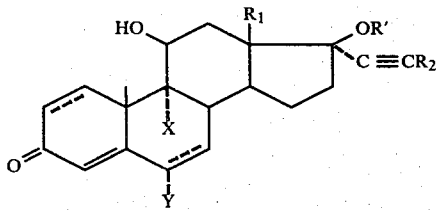

wherein $R_1$ is alkyl of 1 to 3 carbon atoms, R' is an acyl of an organic carboxylic acid or carbonic acid of 1 to 18 carbon atoms, $R_2$ is selected from the group consisting of alkyl of 1 to 12 carbon atoms, alkenyl of 2 to 12 carbon atoms, —$CF_3$, aryl of 6 to 12 carbon atoms and aralkyl of 7 to 12 carbon atoms, Y is selected from the group consisting of hydrogen, fluorine and methyl, X is selected from the group consisting of hydrogen, chlorine, bromine and fluorine and the dotted lines in the A and B rings indicate one or 2 double bonds in 1(2) and 6(7) positions with the proviso when $R_1$ is methyl and the B ring is saturated X is hydrogen when Y is hydrogen and X is not hydrogen when Y is fluorine.

Among the preferred compounds of the invention are compounds of the formula

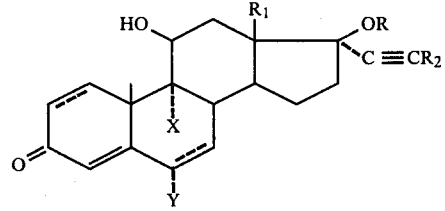

wherein $R_1$, $R_2$, X and Y have the above definitions and R is an acyl of an organic carboxylic acid of 1 to 18 carbon atoms.

Examples of suitable acids for the acyl of R are saturated and unsaturated aliphatic and cycloaliphatic carboxylic acids, especially alkanoic acids. Specific alkanoic acids are formic acid, acetic acid, propionic acid, butyric acid, isobutyric acid, valeric acid, undecylic acid, hydroxy alkanoic acids such as hydroxy acetic acid. Cycloalkyl carboxylic acids and cycloalkanoic acids are cyclopropyl carboxylic acid, cyclopentyl carboxylic acid, cyclohexyl carboxylic acid, cyclopentylacetic acid, cyclopentylpropionic acid, cyclohexylacetic acid and cyclohexylpropionic acid. Also useful are benzoic acid, phenylalkanoic acids such as phenylacetic acid or phenylpropionic acid and amino acids such as aspartic acid or diethylaminoacetic acid.

Examples of values for R' other than those of R are acyls of organic carbonic acids, especially alkoxycarbonyl and alkenylcarbonyl groups optionally substituted and cycloalkoxycarbonyl groups such as methoxycarbonyl, ethoxycarbonyl, cyclohexylmethoxycarbonyl, dicyclohexylmethoxycarbonyl, vinyloxycarbonyl and isopropenyloxycarbonyl.

Examples of $R_1$ are methyl, ethyl, propyl and isopropyl, preferably methyl or ethyl. Examples of $R_2$ are alkyl such as methyl, ethyl, n-propyl, isopropyl, n-butyl, isobutyl, n-pentyl, n-hexyl, 2-methyl-pentyl, 2,3-dimethyl-butyl and 2,2-dimethyl-hexyl; alkenyl such as vinyl, isopropenyl, isobutenyl, allyl and 2-methyl-allyl; aryl such as phenyl and aralkyl such as benzyl and phenethyl.

Among the preferred compounds of formula I' are those wherein $R_1$ is methyl, those wherein the A ring has a double bond in the 1(2) position, those wherein the B ring is saturated, those wherein Y is hydrogen, those wherein X is hydrogen and those wherein $R_2$ is alkyl of 1 to 4 carbon atoms, especially methyl, or alkenyl of 2 to 4 carbon atoms. Especially preferred are compounds of the formula

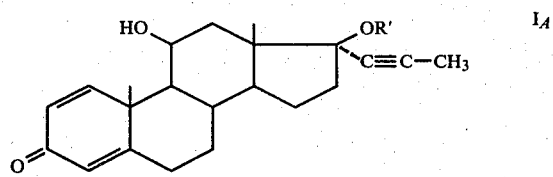

wherein R' has the above definition.

The novel process of the invention comprises reacting a compound of the formula

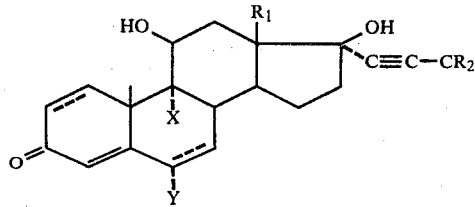

wherein $R_1$, $R_2$, X, Y and the dotted lines have the above definition with an esterification agent of an acid of the formula R'—OH to selectively acylate the 17-hydroxyl.

A preferred esterification agent for the process comprises a compound of the formula

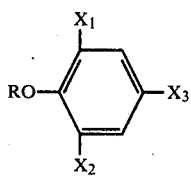

wherein R has the above definition and $X_1$, $X_2$ and $X_3$ are individually selected from the group consisting of hydrogen and nitro with at least one X being nitro. Particularly preferred is the agent wherein all the Xs are nitro which can be formed in situ by reacting picric acid with a compound of the formula R—Hal wherein R has the above definition and Hal is halogen, preferably chlorine.

Another preferred esterification agent for the process is a compound of the formula $R_1'$—Hal wherein Hal is chlorine or bromine and $R_1'$ is an acyl of an organic carbonic acid of 1 to 18 carbon atoms and the reaction is preferably effected in the presence of a basic agent such as pyridine or an alkali metal hydride.

Another process for the preparation of a compound of formula I' comprises reacting a compound of the formula

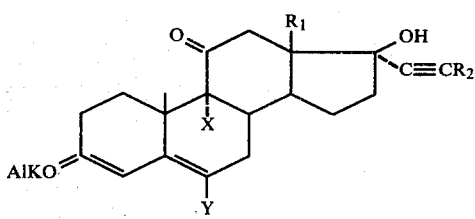

wherein $R_1$, $R_2$, X and Y have the above definition and AlK alkyl of 1 to 12 carbon atoms with an esterification agent obtain a compound of the formula

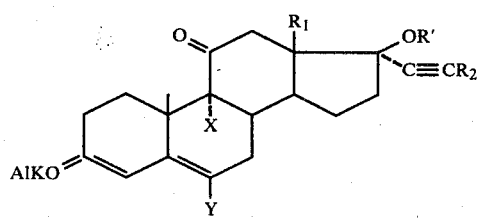

wherein $R_1$, $R_2$, R', X, Y and ALK have the above definitions, reacting the latter with a reducing agent to obtain a compound of the formula

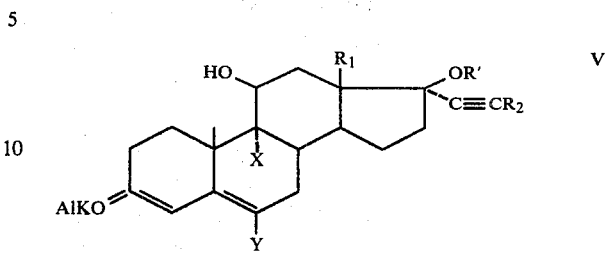

and reacting the latter with either an acid hydrolysis agent or an agent capable of freeing the ketone group and creating a $\Delta^{4,6}$-system or with an agent capable of freeing the ketone group and creating a $\Delta^{1,4,6}$-system to obtain the compounds of formula I'.

In a preferred mode of the latter process, the esterification is effected with a preferred esterification agent as mentioned above or with an organic carboxylic acid or a functional derivative thereof such as its acid chloride or acid anhydride under classical conditions and the reducing agent is an alkali metal borohydride. The acid hydrolysis agent is preferably hydrochloric acid, sulfuric acid, acetic acid, citric acid or p-toluene sulfonic acid. The agent capable of freeing the ketone group creating the $\Delta^{4,6}$-double bond system is preferably a p-benzoquinone such as chloranil and 2,3-dichloro-5,6-dicyano-benzoquinone and the reaction is preferably effected in aqueous acetone but also useful is a biochemical treatment to create the $\Delta^{4,6}$-system such as Arthrobacter Simplex bacteria. The agent to free the ketone group and to create the $\Delta^{1,4,6}$-system is preferably a p-benzoquinone such as chloranil or 2,3-dichloro-5,6-dicyano-benzoquinone in benzene.

The starting materials of formula II may be prepared by reacting a compound of the formula

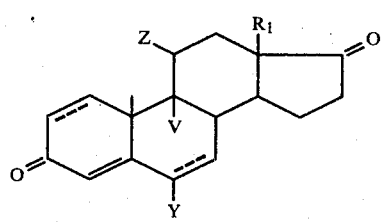

wherein $R_1$, Y and the dotted lines have the above meaning, Z and V may be 9$\beta$,11$\beta$-epoxy or Z is 11$\beta$-OH and V is 9$\alpha$-hydrogen with a compound of the formula $$HC\equiv CR_2 \qquad VI$$

wherein $R_2$ has the above definition in the presence of a tertiary alcoholate to obtain a compound of the formula

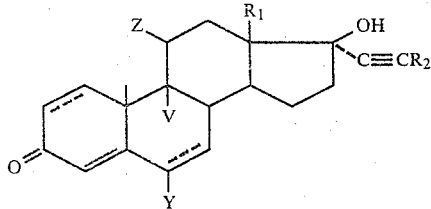

and when Z and V are epoxy, reacting the latter with a compound of the formula H—X₁ wherein X₁ is chlorine, bromine or fluorine to obtain a compound of the formula

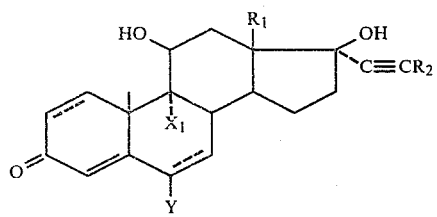

II_B

The preferred compounds of formula V' have the formula

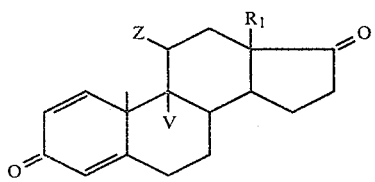

and the alkali metal tert.-alcoholate is preferably an alkali metal tert-butylate or tert.-amylate such as sodium, potassium or lithium tert.-butylate and tert.-amylate.

The starting compounds of formula II may also be prepared by reacting a compound of the formula $$TC \equiv CR_2 \qquad IX$$

wherein T is selected from the group consisting of lithium, potassium and Hal-Mg and Hal is a halogen with a compound of the formula

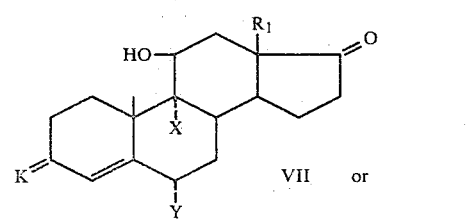

VII or

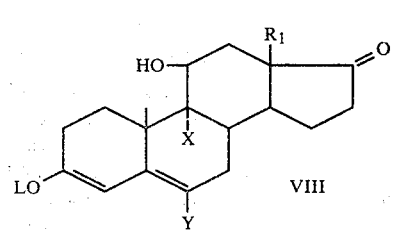

VIII wherein K is a ketal or an oxime, L is alkyl of 1 to 12 carbon atoms and $R_1$, X and Y have the above definitions to obtain a compound of the formula

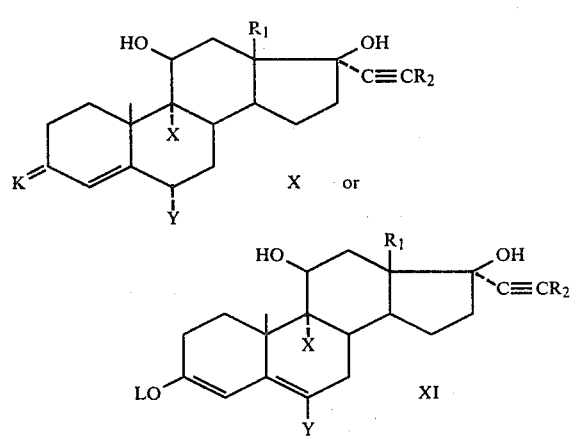

and reacting one of the said compounds with an acid hydrolysis agent to obtain a compound of the formula

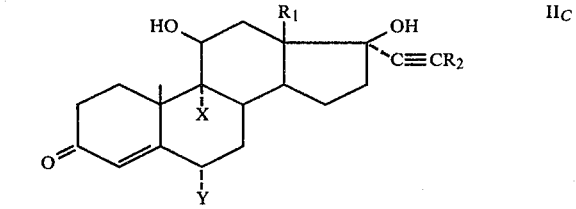

II_C or with an agent capable of freeing the ketone group and creating a $\Delta^{4,6}$-double bond system to obtain a compound of the formula

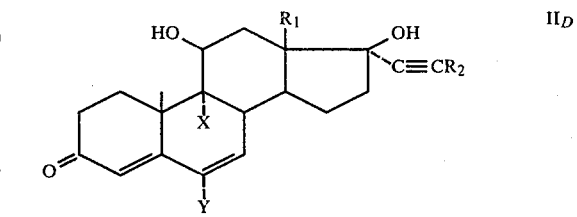

II_D or with an agent capable of freeing the ketone group and creating a $\Delta^{1,4,6}$-double bond system to obtain a compound of the formula

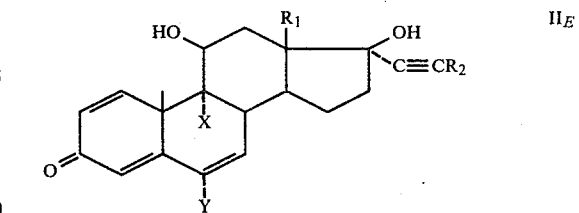

II_E

In this variation of the process, X in formulae VII and VIII is preferably hydrogen. K is preferably alkylenediketal of 2 to 4 carbon atoms such as ehylenediketal or propylene diketal or a dialkyl ketal such as dimethylketal or diethylketal. When K is an oxime, K is preferably —NOH or —NOAlK, wherein AlK is alkyl of 1 to 4 carbon atoms. L is preferably methyl, ethyl or n-propyl and Hal is preferably bromine. The acid hydrolysis agent and the agents to free the ketone group and to form the $\Delta^{4,6}$ or $\Delta^{1,4,6}$-double bond systems are as indicated above.

Some of the compounds of formula II are described in French published patent application No. 2,380,781 and the compounds of formulae V', VII and VIII are generally known and may be prepared by the processes of French Pat. No. 1,359,611 and No. 1,222,424 and U.S. Pat. No. 3,010,957 and No. 3,072,684. The compounds of formula III may be prepared from their corresponding 17-one derivatives by the process of U.S. Pat. No. 3,055,917.

3-ethoxy-6-methyl-$\Delta^{3,5}$-androstadiene-11$\beta$-ol-17-one is a novel product and is a part of the invention.

The novel anti-inflammatory compositions of the invention are comprised of an anti-inflammatorily effective amount of at least one compound of formula I' and an inert pharmaceutical carrier or excipient. The compositions may be in the form of tablets, coated tablets, cachets, capsules, granules, emulsions, syrups, suppositories, injectable solutions or suspensions and preferably in the form of pomades, creams, gels and aerosol preparations. Particularly preferred compositions are those containing 17$\beta$-acetoxy-17$\alpha$-(prop-1-ynyl)-$\Delta^{1,4}$-androstadiene-11$\beta$-ol-3-one or 17$\beta$-propionyloxy-17$\alpha$-(prop-1-ynyl)-$\Delta^{1,4}$-androstadiene-11$\beta$-ol-3-one.

Example of suitable excipients are talc, lactose, arabic gum, cacao butter, magnesium stearate, aqueous and non-aqueous vehicles, fatty bodies of animal or vegetable origin, paraffinic derivatives, glycols, wetting agents, dispersants or emulsifiers and preservatives.

The compositions are useful for the treatment of inflammatory reactions, especially local inflammations such as edemas, dermatosis, pruritsis, diverse forms of eczema and solair erythema.

The novel method of the invention for treating inflammation in warm-blooded animals, including humans, comprises administering to warm-blooded animals an anti-inflammatorily effective amount of at least one compound of formula I. The compounds may be administered orally, rectally or parenterally but most preferably topically. The usual daily dose is 0.2 to 20 mg/kg depending on the compound and the method of administration. When applied topically for example, the compound of Example 2 may be applied 1 to 4 times a day in the form of a pomade containing 0.1 to 5% by weight of the said compound.

In the following examples there are described several preferred embodiments to illustrate the invention. However, it is to be understood that the invention is not intended to be limited to the specific embodiments.

EXAMPLE 1

17$\alpha$-(prop-1-ynyl)-17$\beta$-valeroyloxy-$\Delta^{1,4}$-androstadiene-11$\beta$-ol-3-one 0.79 ml of valeroyl chloride and 0.6 ml of pyridine were added to a solution of 1.68 g of picric acid in 20 ml of methylene chloride and after stirring the mixture at room temperature for 10 minutes, 2 g of 17$\alpha$-(prop-1-ynyl)-$\Delta^{1,4}$-androstadiene-11$\beta$,17$\beta$-diol-3-one were added thereto. The mixture was stirred at room temperature for 68 hours and was then poured into an aqueous saturated sodium bicarbonate solution. The mixture was extracted with methylene chloride and the organic phase was washed with aqueous saturated sodium bicarbonate solution, dried and evaporated to dryness to obtain 2.9 g of residue. The latter was chromatographed over silica gel and was eluted with a 1-1 benzene-ethyl acetate mixture to obtain 1.7 g of product which was crystallized from methanol to obtain 941 mg of 17$\alpha$-(prop-1-ynyl)-17$\beta$-valeroyloxy-$\Delta^{1,4}$-androstadiene-11$\beta$-ol-3-one melting at 194° C.

EXAMPLE 2

17$\beta$-acetoxy-17$\alpha$-(prop-1-ynyl)-$\Delta^{1,4}$-androstadiene-11$\beta$-ol-3-one Using the procedure of Example 1, 1.68 g of picric acid, 0.47 ml of acetyl chloride and 2 g of 17$\alpha$-(prop-1-ynyl)-$\Delta^{1,4}$-androstadiene-11$\beta$,17$\beta$-diol-3-one were reacted and after stirring for 5 days, 1.57 g of product were obtained. The latter was crystallized from isopropyl ether to obtain 1.033 g of 17$\beta$-acetoxy-17$\alpha$-(prop-1-ynyl)-$\Delta^{1,4}$-androstadiene-11$\beta$-ol-3-one melting at 239° C.

EXAMPLE 3

17$\beta$-propionyloxy-17$\alpha$-(prop-1-ynyl)-$\Delta^{1,4}$-androstadiene-11$\beta$-ol-3-one Using the procedure of Example 1, 1.68 g of picric acid, 0.58 ml of propionyl chloride and 2 g of 17$\alpha$-(prop-1-ynyl)-$\Delta^{1,4}$-androstadiene-11$\beta$,17$\beta$-diol-3-one were reacted and after stirring the reaction mixture 92 hours, 1.35 g of product were obtained. Crystallization of the latter from methanol yielded 997 mg of 17$\beta$-propionyloxy-17$\alpha$-(prop-1-ynyl)-$\Delta^{1,4}$-androstadiene-11$\beta$-ol-3-one melting at 214° C.

EXAMPLE 4

17$\beta$-butyryloxy-17$\alpha$-(prop-1-ynyl)-$\Delta^{1,4}$-androstadiene-11$\beta$-ol-3-one Using the procedure of Example 1, 1.68 g of picric acid, 0.686 ml of butyryl chloride and 2 g of 17$\alpha$-(prop-1-ynyl)-$\Delta^{1,4}$-androstadiene-11$\beta$,17$\beta$-diol-3-one were reacted and after stirring for 4 days, 1.205 g of product were obtained which was crystallized from a methylene chloride-isopropyl ether mixture to obtain 1.12 g of 17$\beta$-butyryloxy-17$\alpha$-(prop-1-ynyl)-$\Delta^{1,4}$-androstadiene-11$\beta$-ol-3-one melting at 205° C.

EXAMPLE 5

17$\beta$-(3-methyl-1-oxo-butyloxy)-17$\alpha$-(prop-1-ynyl)-$\Delta^{1,4}$-androstadiene-11$\beta$-ol-3-one Using the procedure of Example 1, 1.68 g of picric acid, 0.819 ml of isovaleryl chloride and 2 g of 17$\alpha$-(prop-1-ynyl)-$\Delta^{1,4}$-androstadiene-11$\beta$,17$\beta$-diol-3-one were reacted, and after stirring the mixture for 4 days, 1.44 g of product were obtained which was crystallized from a methylene chloride-isopropyl ether mixture to obtain 1.240 g of 17$\beta$-(3-methyl-1-oxo-butyloxy)-17$\alpha$-(prop-1-ynyl)-$\Delta^{1,4}$-androstadiene-11$\beta$-ol-3-one melting at 214° C.

EXAMPLE 6

17$\beta$-(ethoxycarbonyloxy)-17$\alpha$-(prop-1-ynyl)-$\Delta^{1,4,6}$-androstatriene-11$\beta$-ol-3-one 1.84 g of 3-ethoxy-21-methyl-$\Delta^{3,5}$-pregnadiene-20-yne-17$\beta$-ol-11-one were added under an inert gas to a suspension of 240 mg of sodium hydride in the form of 55% in mineral oil in 10 ml of tetrahydrofuran and the mixture was refluxed for 30 minutes and then was cooled to 0° C. 1 ml of ethyl chloroformate was added to the mixture which was held at 0° C. for 30 minutes and was then poured into an aqueous sodium bicarbonate solution. The mixture was extracted with ether and the ether extract was dried and evaporated to dryness. A solution of 2.5 g of the residue in 40 ml of dimethylformamide containing 10% of water was admixed with 2 g of potassium borohydride and 2 g of phenol and the mixture was stirred for 22 hours. Another 1 g of potassium borohydride and 1 g of phenol were added thereto and the mixture was stirred for another 24 hours. The mixture was poured into 500 ml of an ice-water mixture and the mixtue was stirred for 2 hours and was then vacuum filtered. The recovered product was washed with water, with aqueous sodium bicarbonate solution and with water and was dried.

A solution of the resulting product in 30 ml of benzene was added to a solution of 5 g of 2,3-dichloro-5,6-dicyano-benzoquinone in 70 ml of benzene and the mixture was stirred at 20° C. for 30 minutes and was then poured into an aqueous sodium bicarbonate solution. The mixture was extracted with ether and the ether extract was washed with 0.5 N sodium thiosulfate solution, with aqueous sodium bicarbonate and was dried and evaporated to dryness. The residue was chromatographed over silica gel and elution with a 7–3 benzene-ethyl acetate mixture yielded a product which was crystallized from isopropyl ether to obtain 260 mg of 17$\beta$-(ethoxycarbonyloxy)-17$\alpha$-(prop-1-ynyl)-$\Delta^{1,4,6}$-androstatriene-11$\beta$-ol-3-one melting at 140° C. and a specific rotation of $[\alpha]_D^{20} = -80° \pm 2.5°$ (c=0.7% in CHCl$_3$).

Analysis: C$_{25}$H$_{30}$O$_5$; molecular weight=410.49: Calculated: %C,73.14; %H,7.37. Found: %C,72.9; %H,7.5.

17$\alpha$-(prop-1-ynyl)-$\Delta^{1,4,6}$-androstatriene-11$\beta$,17$\beta$-diol-3-one was directly esterified with ethyl chloroformate in the presence of sodium hydride to obtain 17$\alpha$-(ethoxycarbonyloxy)-17$\beta$-(prop-1-ynyl)-$\Delta^{1,4,6}$-androstatriene-11$\beta$-ol-3-one identical to the above product.

EXAMPLE 7

21-methyl-$\Delta^{4,6}$-pregnadiene-20-yne-11$\beta$,17$\beta$-diol-3-one

STEP A:
3-ethoxy-21-methyl-$\Delta^{3,5}$-pregnadiene-20-yne-11$\beta$,17$\beta$-diol Propyne was bubbled for 2 hours through 70 ml of a solution of 0.75 M of ethyl magnesium bromide in tetrahydrofuran at 0° C. and the temperature was then allowed to rise to room temperature. A mixture of 3.45 g of 3-ethoxy-$\Delta^{3,5}$-and-rostadiene-11$\beta$-ol-17-one and 14 ml of dry tetrahydrofuran were added to the reaction mixture and the mixture was stirred at 20°–25° C. for 45 minutes. The mixture was poured into a cold ammonium chloride solution and the mixture was extracted with ether. The ether extract was washed with aqueous saturated sodium bicarbonate solution, dried over sodium sulfate and evaporated to dryness under reduced pressure to obtain 3-ethoxy-21-methyl-$\Delta^{3,5}$-pregnadiene-20-yne-11$\beta$,17$\beta$-diol which was used as is for the next step.

STEP B:
21-methyl-$\Delta^{4,6}$-pregnadiene-20-yne-11$\beta$,17$\beta$-diol-3-one 5 ml of distilled water were added to a solution of 4 g of the product of Step A in 100 ml of acetone and 4.8 g of 2,3-dichloro-5,6-dicyano-benzoquinone were added to the mixture which was then stirred for one hour at room temperature. The mixture was poured into aqueous saturated sodium bicarbonate solution and the mixture was extracted with methylene chloride. The organic phase was washed with 0.5 M sodium thiosulfate solution, dried over sodium sulfate and was evaporated to dryness. The 3.8 g of residue was chromatographed over silica gel and was eluted with a 1–1 benzene-ethyl acetate mixture to obtain a product with an Rf=0.25. The latter was crystallized from isopropyl ether to obtain 21-methyl-$\Delta^{4,6}$-pregnadiene-20-yne-11$\beta$,17$\beta$-diol-3-one melting at 200° C.

Analysis: C$_{22}$H$_{28}$O$_3$; molecular weight=340.466: Calculated: %C,77.6; %H,8.29. Found: %C,77.8; %H,8.3.

EXAMPLE 8

21-methyl-$\Delta^{1,4,6}$-pregnatriene-20-yne-11$\beta$,17$\beta$-diol-3-one

A solution of 3.7 g of 3-ethoxy-21-methyl-$\Delta^{3,5}$-pregnadiene-20-yne-11$\beta$,17$\beta$-diol in 50 ml of benzene was poured under nitrogen with stirring into a solution of 6.8 g of 2,3-dichloro-5,6-dicyano-benzoquinone in benzene and the mixture was stirred for 25 minutes. The mixture was washed with aqueous saturated sodium bicarbonate solution and then with 0.5 M sodium thiosulfonate solution, dried over sodium sulfate and evaporated to dryness under reduced pressure. The 2.75 g of residue was chromatographed over silica gel and was eluted with a 1–1 benzene-ethyl acetate mixture to obtain 1.2 g of product with an Rf=0.20. The latter was crystallized from an isopropyl ether-acetone-methylene chloride mixture to obtain 819 mg of 21-methyl-$\Delta^{1,4,6}$-pregnatriene-20-yne-11$\beta$,17$\beta$-diol-3-one melting at 216° C.

Analysis: C$_{22}$H$_{26}$O$_3$: molecular weight=338.45: Calculated: %C,78.07; %H,7.74. Found: %C,77.9; %H,7.7.

EXAMPLE 9

21-phenyl-$\Delta^{1,4}$-pregnadiene-20-yne-11$\beta$,17$\beta$-diol-3-one

A mixture of 2.91 g of potassium tert.-butylate, 2.75 ml of phenylactylene and 100 ml of dioxane was stirred at room temperature for one hour and then a mixture of 3 g of $\Delta^{1,4}$-androstadiene-11$\beta$-ol-3,17-dione (prepared by the process of U.S. Pat. No. 3,010,957) in 30 ml of dioxane was added thereto. The mixture was stirred for 2 hours and an aqueous acetic acid solution was added thereto. The mixture was diluted with water and was then extracted with methylene chloride. The organic phase was washed with aqueous saturated sodium bicarbonate solution, dried over sodium sulfate and evaporated to dryness to obtain 4.25 g of residue. The latter was chromatographed over silica gel and was eluted with a 6–4 benzene-ethyl acetate mixture to obtain 1.265 g of product with an Rf=0.20. The latter was crystallized from a methylene chloride-isopropyl ether mixture to obtain 21-phenyl-$\Delta^{1,4}$-pregnadiene-20-yne-11$\beta$,17$\beta$-diol-3-one melting at 262° C. and having a specific rotation of $[\alpha]_D^{20} = -21° \pm 2°$ (c=0.7% in CHCl$_3$).

EXAMPLE 10

21-trifluoromethyl-$\Delta^{1,4}$-pregnadiene-20-yne-11$\beta$,17$\beta$-diol-3-one A current of trifluoromethylacetylene was bubbled with stirring under a nitrogen atmosphere through a solution of 2.1 g of $\Delta^{1,4}$-androstadiene-11$\beta$-ol-3,17-dione, 3.5 ml of hexametyhylphosphortriamide and 35 ml of anhydrous tetrahydrofuran cooled to −70° C. and then a solution of 3.4 g of 96% potassium tert.-butylate, 70 ml of tetrahydrofuran and 3.5 ml of hexamethylphosphortriamide was added thereto dropwise. The mixture was poured into an aqueous ammonium chloride solution and the mixture was extracted with ether. The ether extract was dried and evaporated to dryness and the residue was chromatographed over silica gel. Elution with a 6-4 benzene-ethyl acetate mixture yielded 2.7 g of product which was crystallized from a methylene chloride-isopropyl ether mixture to obtain 2.248 g of 21-trifluoromethyl-$\Delta^{1,4}$-pregnadiene-20-yne-11$\beta$,17$\beta$-diol-3-one melting at 254°-255° C. and having a specific rotation of $[\alpha]_D^{20} = -6.5° \pm 1.5°$ (c=0.75% in CHCl$_3$).

EXAMPLE 11

6$\alpha$,21-dimethyl-$\Delta^{1,4}$-pregnadiene-20-yne-11$\beta$,17$\beta$-diol-3-one Propyne was bubbled for 90 minutes through a solution of 200 ml of tetrahydrofuran and 10.3 g of 96% potassium tert.-butylate and the mixture was then stirred for a few hours after which 20 ml of hexamethylphosphortriamide were added thereto. The mixture was cooled to $-15°$ C. and a solution of 5.75 g of 6$\alpha$-methyl-$\Delta^{1,4}$-androstadiene-11$\beta$-ol-3,17-dione (prepared by process of French Pat. No. 1,359,611) in 60 ml of tetrahydrofuran was added thereto at $-15°$ C. The mixture was stirred at $-15°$ C. for 4 hours and was then poured into aqueous hydrochloric acid. The mixture was extracted with ether and the ether phase was washed with water, dried and evaporated to dryness to obtain 6.05 g of residue. The latter was chromatographed over silica gel and was eluted with an 8-2 methylene chloride-acetone mixture. The product was chromatographed over silica gel a second time and was eluted with a 6-4 benzene-ethyl acetate mixture. The product was crystallized from isopropyl ether to obtain 1.105 g of 6$\alpha$,21-dimethyl-$\Delta^{1,4}$-pregnadiene-20-yne-11$\beta$,17$\beta$-diol-3-one melting at 196° C. and having a specific rotation of $[\alpha]_D^{20} = -14° \pm 2°$ (c=0.5% in CHCl$_3$).

EXAMPLE 12

6,21-dimethyl-$\Delta^{4,6}$-pregnadiene-20-yne-11$\beta$,17$\beta$-diol-3-one

A current of propyne was bubbled with stirring at 0° C. through a solution of 1.15 M of ethyl magnesium bromide in tetrahydrofuran under nitrogen and the temperature was allowed to rise to room temperature. The mixture was stirred for 90 minutes and 6.3 g of 3-ethoxy-6-methyl-$\Delta^{3,5}$-androstadiene-11$\beta$-ol-17-one were added thereto. The mixture was stirred another 90 minutes and was then poured into aqueous ammonium chloride solution. The iced mixture was extracted with ether and the ether phase was washed with aqueous sodium bicarbonate solution, was dried and evaporated to dryness under reduced pressure. The 4.7 g of residue was dissolved in 100 ml of acetone and 5 ml of water and 2.5 g of 2,3-dichloro-5,6-dicyano-benzoquinone were added thereto. The reaction mixture was poured into aqueous sodium bicarbonate solution and the mixture was extracted with methylene chloride. The organic phase was washed with sodium thiosulfate solution, dried over sodium sulfate and was evaporated to dryness under reduced pressure. The residue was chromatographed over silica gel and was eluted with a 1—1 benzeneethyl acetate mixture to obtain 2.95 g of 6,21-dimethyl-$\Delta^{4,6}$-pregnadiene-20-yne-11$\beta$,17$\beta$-diol-3-one.

RMN Spectrum (CDCl$_3$-60 MHz): Peaks at 81.5, 71.5 and 110 Hz (CH$_3$); at 270 Hz (H); at 352 Hz (ethylenic H).

Analysis: C$_{23}$H$_{30}$O$_3$; molecular weight=354.47: Calculated: %C, 76.76; %H, 8.57. Found: %C, 76.6; %H, 8.7.

EXAMPLE 13

21-phenyl-$\Delta^4$-pregnene-20-yne-11$\beta$,17$\beta$-diol-3-one 7.2 ml of phenylacetylene were added dropwise at 0° C. to a solution of 40 ml of anhydrous tetrahydrofuran and 40 ml of a solution of 1.3 M of n-butyllithium in hexane and then 3 g of 3-ethoxy-$\Delta^{3,5}$-androstadiene-11$\beta$-ol-17-one were added thereto. The mixture was stirred at room temperature for 17 hours and was then poured into aqueous ammonium chloride solution. The mixture was extracted with ether and the ether phase was chromatographed over silica gel. Elution with a 1—1 benzene-ethyl acetate mixture containing 0.2% of triethylamine yielded a product with an Rf=0.35 which was then treated for 30 minutes with a solution of 125 ml of methanol and 25 ml of N hydrochloric acid. The mixture was poured into water and the mixture was extracted with methylene chloride. The organic phase was dried over sodium sulfate and was evaporated to dryness. The residue was chromatographed over silica gel to obtain 1.1 g of 21-phenyl-$\Delta^4$-pregnene-20-yne-11$\beta$,17$\beta$-diol-3-one with a specific rotation of $[\alpha]_D^{20} = -4° \pm 2°$ (c=0.7% in CHCl$_3$).

EXAMPLE 14

9$\alpha$-fluoro-21-methyl-$\Delta^{1,4}$-pregnadiene-20-yne-11$\beta$,17$\beta$-diol-3-one

STEP A:

9$\beta$,11$\beta$-epoxy-21-methyl-$\Delta^{1,4}$-pregnadiene-20-yne-17$\beta$-ol-3-one Propyne was bubbled through a solution of 15.6 g of 96% potassium tert.-butylate in 600 ml of tetrahydrofuran for 90 minutes and then a solution of 4 g of 9$\beta$,11$\beta$-epoxy-$\Delta^{1,4}$-androstadiene-3,17-dione (prepared by process of French Pat. No. 1,222,424) in 40 ml of tetrahydrofuran was added thereto. The mixture was stirred for 3 days and then 30 ml of 6 N hydrochloric acid were added thereto. The mixture was stirred for 30 minutes and was poured into water and the mixture was extracted with ether. The ether pase was washed with water, dried over sodium sulfate and evaporated to dryness under reduced pressure to obtain 4.5 g of 9$\beta$,11$\beta$-epoxy-21-methyl-$\Delta^{1,4}$-pregnadiene-20-yne-17$\beta$-ol-3-one which was used as is for the next step.

STEP B:

9$\alpha$-fluoro-21-methyl-$\Delta^{1,4}$-pregnadiene-20-yne-11$\beta$,17$\beta$-diol-3-one A complex of 45 ml of dimethylformamide and hydrofluoric acid was poured into a solution of the product of Step A in 45 ml of dimethylformamide at $-40°$ C. and the temperature was allowed to rise to room temperature. The mixture was stirred for 48 hours at room temperature and was then poured into a solution of water, ice and ammonium hydroxide. The mixture was vacuum filtered and the product was washed with water until neutral to obtain 3.5 g of product. The filtrate was extracted with ether to obtain another 1.1 g of product. The combined products were chromatographed over silica gel and were eluted with a 6—4 benzene-ethyl acetate mixture and then with an 8—2 methylene chloride-isopropyl ether mixture to obtain 1.115 g of 9α-fluoro-21-methyl-Δ$^{1,4}$-pregnadiene-20-yne-11β,17β-diol-3-one melting at 220° C. and having a specific rotation of $[\alpha]_D^{20} = -2.5° \pm 2°$ (c=0.5% in CHCl$_3$).

Analysis: C$_{22}$H$_{27}$O$_3$F; molecular weight=358.45: Calculated: %C, 73.71; %H, 7.59; %F, 5.29. Found: %C, 73.5; %H, 7.7; %F, 5.0.

EXAMPLE 15

3-ethoxy-Δ$^{3,5}$-androstadiene-11α-ol-17-one

A mixture of 43 g of Δ$^4$-androstene-11β-ol-3,17-dione (U.S. Pat. No. 3,072,684), 215 ml of ethanol and 43 ml of 0.26 M ethyl orthoformate solution was heated to 50° C. and then 5.2 ml of a solution of 0.48 g of p-toluene sulfonic acid in 50 ml of ethanol was added thereto. The resulting solution was held at 50° C. for 5 minutes and then 8.6 ml of triethylamine were added thereto. The mixture was cooled to 20° C. and then 258 ml of water were added thereto. The mixture was cooled to 0° to 5° C. and was filtered and the recovered product was washed with a 50—50—0.5 ethanol-water-pyridine mixture to obtain 40.1 g of 3-ethoxy-Δ$^{3,5}$-androstadiene-11β-ol-17-one.

EXAMPLE 16

3-ethoxy-6-methyl-Δ$^{3,5}$-androstadiene-11β-ol-17-one

A suspension of 1.80 g of 6α-methyl-Δ$^4$-androstene-11β-ol-3,17-dione, 10 ml of ethanol and 2 ml of triethoxymethane was stirred under nitrogen at 50° C. and then 0.25 ml of a solution of 480 mg of p-toluene sulfonic acid in 50 ml of ethanol were added thereto. After 5 minutes of stirring, 0.4 ml of triethylamine were added thereto and the mixture was cooled in an ice bath. Water was added dropwise to the mixture which was then vacuum filtered. The recovered product was washed with a 7—3 ethanol-water mixture and was dried to obtain 1.66 g of 3-ethoxy-6-methyl-Δ$^{3,5}$-androstadiene-11β-ol-17-one with an Rf=0.55 (1—1 benzene-ethyl acetate).

EXAMPLE 17

3-ethoxy-21-methyl-Δ$^{3,5}$-pregnadiene-20-yne-17β-ol-11-one

Dry propyne was bubbled for 2 hours through 132 ml of a solution of 1.15 M of ethyl magnesium bromide in tetrahydrofuran cooled to 0° C. and the temperature was raised to 20° C. while maintaining the propyne current. A solution of 20 g of 3-ethoxy-Δ$^{3,5}$-androstadiene-11,17-dione (U.S. Pat. No. 3,055,917) in 80 ml of dry tetrahydrofuran was added to the mixture over 40 minutes and the mixture was stirred for one hour and then poured into an iced ammonium chloride solution. The mixture was extracted with ether and the ether phase was washed with water, dried and evaporated to dryness. The crystals were washed with isopropyl ether containing a few drops of pyridine to obtain 17.7 g of 3-ethoxy-21-methyl-Δ$^{3,5}$-pregnadiene-20-yne-17β-ol-11-one melting at 172° C.

EXAMPLE 18

A pomade for topical application was prepared containing 1 g of the compound of Example 2 and sufficient excipient of lanolin and vaseline to obtain a final weight of 100 g.

PHARMACOLOGICAL DATA

The anti-inflammatory activity for the compounds of Examples 2 and 3 was determined by the edema test of croton inspired by Tonelli et al [Endocrinology, Vol. 77 (1965), p. 625]. In the test, an edema was provoked in mice by application of croton oil to one ear thereof. The mice of the first group received an application of a croton oil solution on the right ear and the mice of a second group received an application of a croton oil solution containing the test product on the right ear. Nothing was applied to the left ear of the mice. After 6 hours, the ears were cut off and were weighed and the difference in the total weight of the left and right ears is the degree of inflammation. At a dose of 0.2 mg/kg, the product of Example 2 and 3 both showed a clear anti-inflammatory activity.

Various modifications of the products and processes of the invention may be made without departing from the spirit or scope thereof and it is to be understood that the invention is intended to be limited only as defined in the appended claims.

What we claim:

1. A Δ$^4$-androstene of the formula

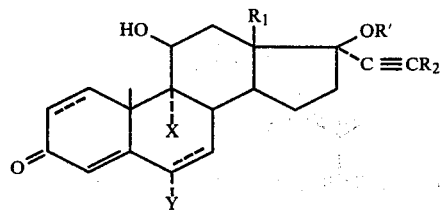

wherein R$_1$ is alkyl of 1 to 3 carbon atoms, R' is an acyl of an organic carboxylic acid or carbonic acid of 1 to 18 carbon atoms, R$_2$ is selected from the group consisting of alkyl of 1 to 12 carbon atoms, alkenyl of 2 to 12 carbon atoms, —CF$_3$, aryl of 6 to 12 carbon atoms and aralkyl of 7 to 12 carbon atoms, Y is selected from the group consisting of hydrogen, fluorine and methyl, X is selected from the group consisting of hydrogen, chlorine, bromine and fluorine and the dotted lines in the A and B rings indicate one or 2 double bonds in 1(2) and 6(7) position with the proviso when R$_1$ is methyl and the B ring is saturated, X is hydrogen when Y is hydrogen and X is not hydrogen when Y is fluorine.

2. A compound of claim 1 wherein R' is an acyl of an organic carboxylic acid of 1 to 18 carbon atoms.

3. A compound of claim 1 wherein R$_1$ is methyl.

4. A compound of claim 1 wherein the A ring has a double bond in the 1(2)-position.

5. A compound of claim 1 wherein the B ring is saturated.

6. A compound of claim 1 wherein Y is hydrogen.

7. A compound of claim 1 wherein X is hydrogen.

8. A compound of claim 1 wherein R$_2$ is selected from the group consisting of alkyl of 1 to 4 carbon atoms and alkenyl of 2 to 4 carbon atoms.

9. A compound of claim 1 wherein R$_2$ is methyl.

10. A compound of claim 1 having the formula

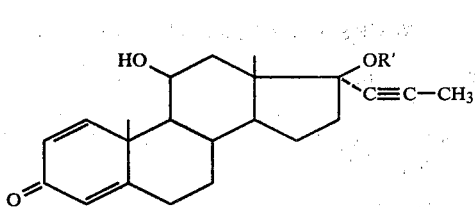

wherein R' has the definition of claim 1.

11. An anti-inflammatory composition comprising an anti-inflammatorily effective amount of at least one compound of claim 1 and an excipient.

12. A composition of claim 11 wherein R' is acyl of an organic carboxylic acid of 1 to 18 carbon atoms.

13. A composition of claim 11 wherein $R_1$ is methyl.

14. A composition of claim 11 wherein the A ring has a double bond in the 1(2)-position.

15. A composition of claim 11 wherein the B ring is saturated.

16. A composition of claim 11 wherein Y is hydrogen.

17. A composition of claim 11 wherein X is hydrogen.

18. A composition of claim 11 wherein $R_2$ is selected from the group consisting of alkyl of 1 to 4 carbon atoms and alkenyl of 2 to 4 carbon atoms.

19. A composition of claim 11 wherein $R_2$ is methyl.

20. A composition of claim 11 having the formula

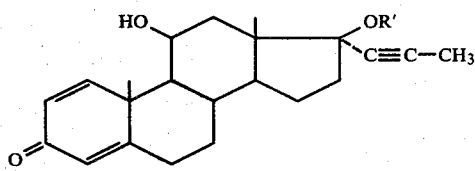

wherein R' has the definition of claim 1.

21. A method of relieving inflammation in warm-blooded animals comprising administering to warm-blooded animals an anti-inflammatorily effective amount of at least one compound of claim 1.

22. A method of claim 21 wherein R' is an acyl of an organic carboxylic acid of 1 to 18 carbon atoms.

23. A method of claim 21 wherein $R_1$ is methyl.

24. A method of claim 21 wherein the A ring has a double bond in the 1(2)-position.

25. A method of claim 21 wherein the B ring is saturated.

26. A method of claim 21 wherein Y is hydrogen.

27. A method of claim 21 wherein X is hydrogen.

28. A method of claim 21 wherein $R_2$ is selected from the group consisting of alkyl of 1 to 4 carbon atoms and alkenyl of 2 to 4 carbon atoms.

29. A method of claim 21 wherein $R_2$ is methyl.

30. A method of claim 21 having the formula

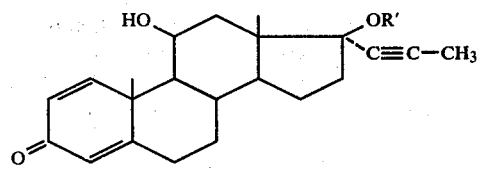

wherein R' has the definition of claim 1.

31. The method of claim 21 wherein the compound is applied topically.

32. A compound of claim 1 which is 17β-acetoxy-17α-(prop-1-ynyl)-$\Delta^{1,4}$-androstadiene-11β-ol-3-one.

33. A compound of claim 1 which is 17β-propionyloxy-17α-(prop-1-ynyl)-$\Delta^{1,4}$-androstadiene-11β-ol-3-one.

* * * * *

UNITED STATES PATENT AND TRADEMARK OFFICE
CERTIFICATE OF CORRECTION

PATENT NO. : 4,232,015
DATED : November 4, 1980
INVENTOR(S) : Jean G. Teutsch et al.

It is certified that error appears in the above—identified patent and that said Letters Patent is hereby corrected as shown below:

Column 1, line 63: After "saturated" insert a comma -- , --.

Column 2, line 33: "alkenylcarbonyl" should read -- alkenyloxycarbonyl --.

Column 10, line 39: "phenylactylene" should read -- phenylacetylene --.

Signed and Sealed this

Fifth Day of May 1981

[SEAL]

Attest:

RENE D. TEGTMEYER

*Attesting Officer*   *Acting Commissioner of Patents and Trademarks*